United States Patent
Pansiera

[19]
[11] Patent Number: 6,080,123
[45] Date of Patent: Jun. 27, 2000

[54] ORTHOTIC JOINT WITH RADIAL HYDRAULIC FORCE TRANSFER

[76] Inventor: Timothy Thomas Pansiera, 31 Teaberry La., Weaverville, N.C. 28787

[21] Appl. No.: 09/153,002

[22] Filed: Sep. 14, 1998

[51] Int. Cl.⁷ ........................................................ A61F 5/00
[52] U.S. Cl. .................................. 602/16; 602/5; 602/26
[58] Field of Search ........................ 602/16–40; 623/26, 623/28, 29, 40–56, 57, 58, 59, 60, 61, 62–64; 403/52, 66, 111, 112, 113, 120, 123, 122, 128, 161, 162, 163, 90, 169, 170, 217; 482/110, 111, 112, 113, 116, 121

[56] References Cited

U.S. PATENT DOCUMENTS

| | | | |
|---|---|---|---|
| 3,631,542 | 1/1972 | Potter | 602/16 |
| 3,799,159 | 3/1974 | Scott | 602/16 |
| 4,657,000 | 4/1987 | Hepburn | 602/16 |
| 4,681,097 | 7/1987 | Pansiera | 602/16 |
| 4,928,676 | 5/1990 | Pansiera | 602/16 |
| 4,958,643 | 9/1990 | Pansiera | 602/16 |
| 5,103,811 | 4/1992 | Crupi, Jr. | 602/16 |
| 5,144,943 | 9/1992 | Luttrell et al. | 602/16 |
| 5,215,508 | 6/1993 | Bastow | 482/79 |
| 5,337,737 | 8/1994 | Rubin et al. | 601/33 |
| 5,352,190 | 10/1994 | Fischer et al. | 602/26 |
| 5,472,412 | 12/1995 | Knoth | 602/26 |
| 5,547,464 | 8/1996 | Luttrell et al. | 602/26 |
| 5,891,061 | 4/1999 | Kaiser | 601/33 |

*Primary Examiner*—Kim M. Lee
*Attorney, Agent, or Firm*—Dorothy S. Morse

[57] ABSTRACT

A joint using a combination of hydraulics and ball bearings to convert liner motion into a radial motion and thereby provide both variable extension assist, as well as an infinite number of flexion stops for controlled flexion flow. Applications may include, but are not limited to, orthotic devices which facilitate the extension and flexion of human joint, such as a knee. The compact configuration of the present invention would provide the cosmetic advantage of allowing such orthotic devices to fit more easily under clothing wherein they would be less noticeable during use.

18 Claims, 5 Drawing Sheets

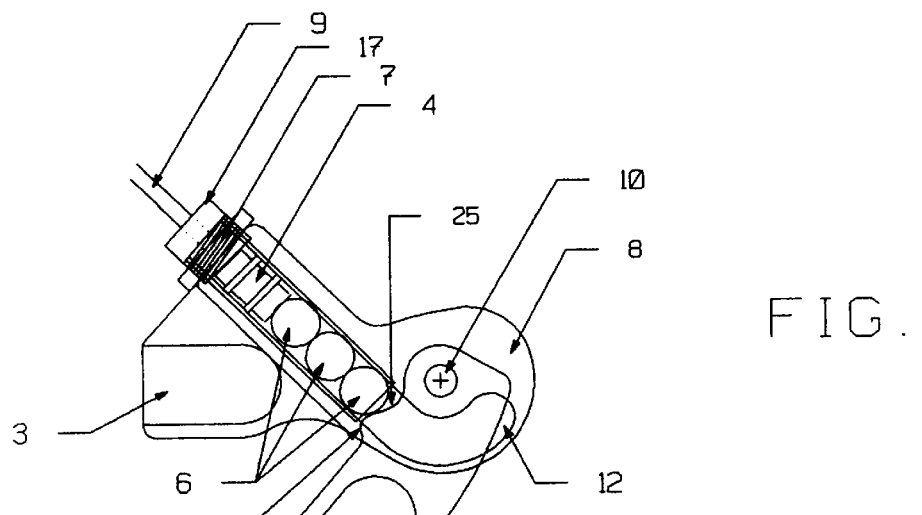
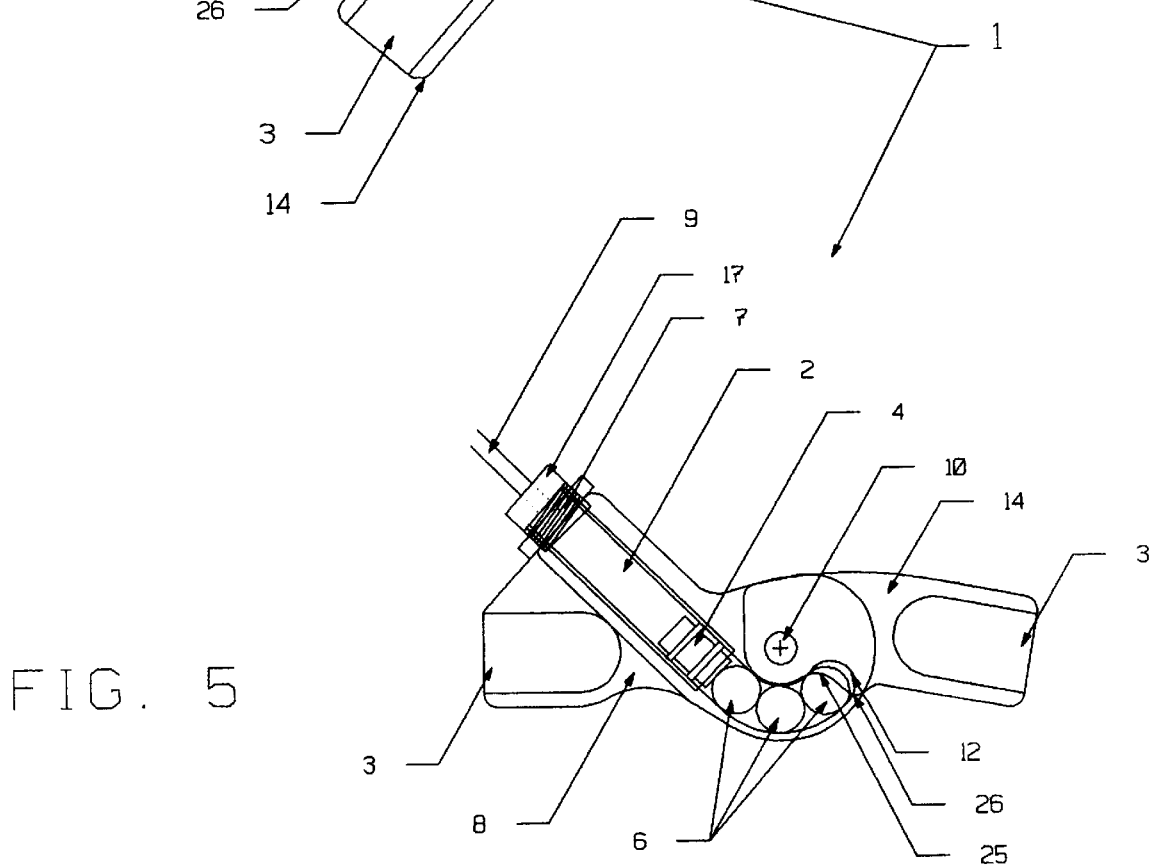

ORTHOTIC JOINT WITH RADIAL HYDRAULIC FORCE TRANSFER

BACKGROUND—FIELD OF INVENTION

This invention relates to joints, specifically to a joint using a combination of hydraulics and ball bearings to convert linear motion into radial motion and thereby provide both variable extension assist, as well as an infinite number of flexion stops for controlled flexion flow. Applications may include, but are not limited to, joints for orthotic devices which facilitate the extension and flexion of a human joint, such as a knee. The compact configuration of the present invention would provide the cosmetic advantage of allowing such orthotic devices to fit more easily under clothing wherein they would be less noticeable during use.

BACKGROUND—DESCRIPTION OF PRIOR ART

Particularly in the field of orthotic devices relating to the support of a human knee, there is a need for a joint which can assist in the forward movement of a person's lower leg and foot, and which will also exhibit a controlled descent once the person's foot is planted on a floor or ground surface and his or her weight is shifted forward over the joint. For social acceptability, it is also desirable to have orthotic devices which are minimally obtrusive. Many joints are known which comprise varying combinations of springs, gears, levers, and cables and which can hold a joint in a limited number of angles of flexion and provide a limited amount of extension assist. However, none provides all of the advantages of the present invention that derive from the combined use of hydraulic forces and ball bearings within a partially arcuate race. It is not known to have a cosmetically advantageous and compactly designed joint which provides adjustable extension assist, as well as an infinite number of flexion stops to prevent sudden collapse of the joint under a shifting weight load, through the combined use of hydraulic forces and ball bearings that radially transfer the linear hydraulic forces applied.

SUMMARY OF INVENTION—OBJECTS AND ADVANTAGES

It is the primary object of this invention to provide a joint which has variable extension assist in combination with an infinite number of flexion stops for controlled flexion flow. It is also an object of this invention to provide a joint which achieves variable extension assist and controlled flexion flow through the introduction of linear hydraulic forces into a partially arcuate race containing ball bearings to radially transfer the hydraulic forces applied. A further object of this invention is to provide a joint which has sufficient strength for use in orthotic devices such as those employed to support a human knee. It is also an object of this invention to provide a compactly configured joint which can help orthotic devices fit more easily under clothing wherein they would be less noticeable during use. Further objects of this invention are to provide a joint made from durable materials in which the amount of extension assist and flexion flow is easily and readily controlled by the user.

As described herein, properly manufactured and connected to cooperating members of a device requiring a joint having at least minimal amounts of extension assist and controlled flexion flow, the present invention would provide a joint which uses hydraulic force in combination with ball bearings to convert applied linear motion into radial motion. Manual control by the user of the amount of hydraulic force introduced into a hydraulically sealed chamber partially filling the ball bearing race provides differing amounts of extension assist, as well as an infinite number of flexion stops. In the preferred embodiment the stationary proximal joint member of the present invention would comprise an elongated race longitudinally therethrough having an arcuate end and a linear end, with the linear end housing a fluid-tight chamber that is in communication with a fluid supply line connected to a hydraulic intensifier. The fluid-tight proximal fluid tube would substantially fill the linear end of the ball bearing race. Also in the preferred embodiment, a heavy duty compression spring in the hydraulic intensifier would help to provide the spring force necessary to increase hydraulic fluid flow into the hollow fluid-tight tube during joint extension. The hydraulic intensifier in combination with the spring in the preferred embodiment of the present invention provides for adjustable compression and variable joint extension assist, while use of a one-way valve and an easy-to-manipulate valve control to adjust the fluid pressure and volume within the fluid-tight tube would determine the resulting flexion response of the joint, which could range from that of fill lock to free action with varying levels of pressure return. The compact design of the present invention which results from the radial hydraulic force transfer would promote social acceptability of the orthotic devices to which it was attached by giving them the cosmetic advantage of being able to fit more easily under clothing wherein they would be less obtrusive during use.

While the description herein provides preferred embodiments of the present invention as it would be used in support of a human knee, such preferred embodiments should not be construed as limiting the scope of the present invention. For example, it is within the contemplation of the present invention to incorporate variations other than those shown and described herein, such as variations in the size and number of ball bearings used; the dimension, configuration, and positioning of the bar slots in the attachment ends of both the proximal joint member and the distal joint member; the means used for securing the pivot points in the proximal and distal joint members to one another; the means of providing spring force for extension assist of the distal joint member relative to the proximal joint member; and the materials from which the proximal and distal joint members, the ball bearings, the hydraulic intensifier, and the other hydraulic components are made. Thus the scope of the present invention should be determined by the appended claims and their legal equivalents, rather than the examples given.

BRIEF DESCRIPTION OF THE DRAWINGS

FIG. 4 is a sectional side view of the preferred embodiment of the present invention having a proximal joint member and a distal joint member pivotally connected to one another, with the rotating distal joint member, ball bearings, and plunger in positions of near maximum flexion.

FIG. 5 is a sectional side view of the preferred embodiment of the present invention having a proximal joint member and a distal joint member pivotally connected to one another, with the rotating distal joint member, ball bearings, and plunger in positions of near maximum extension.

DETAILED DESCRIPTION OF PREFERRED EMBODIMENTS

Figures 1, 8:
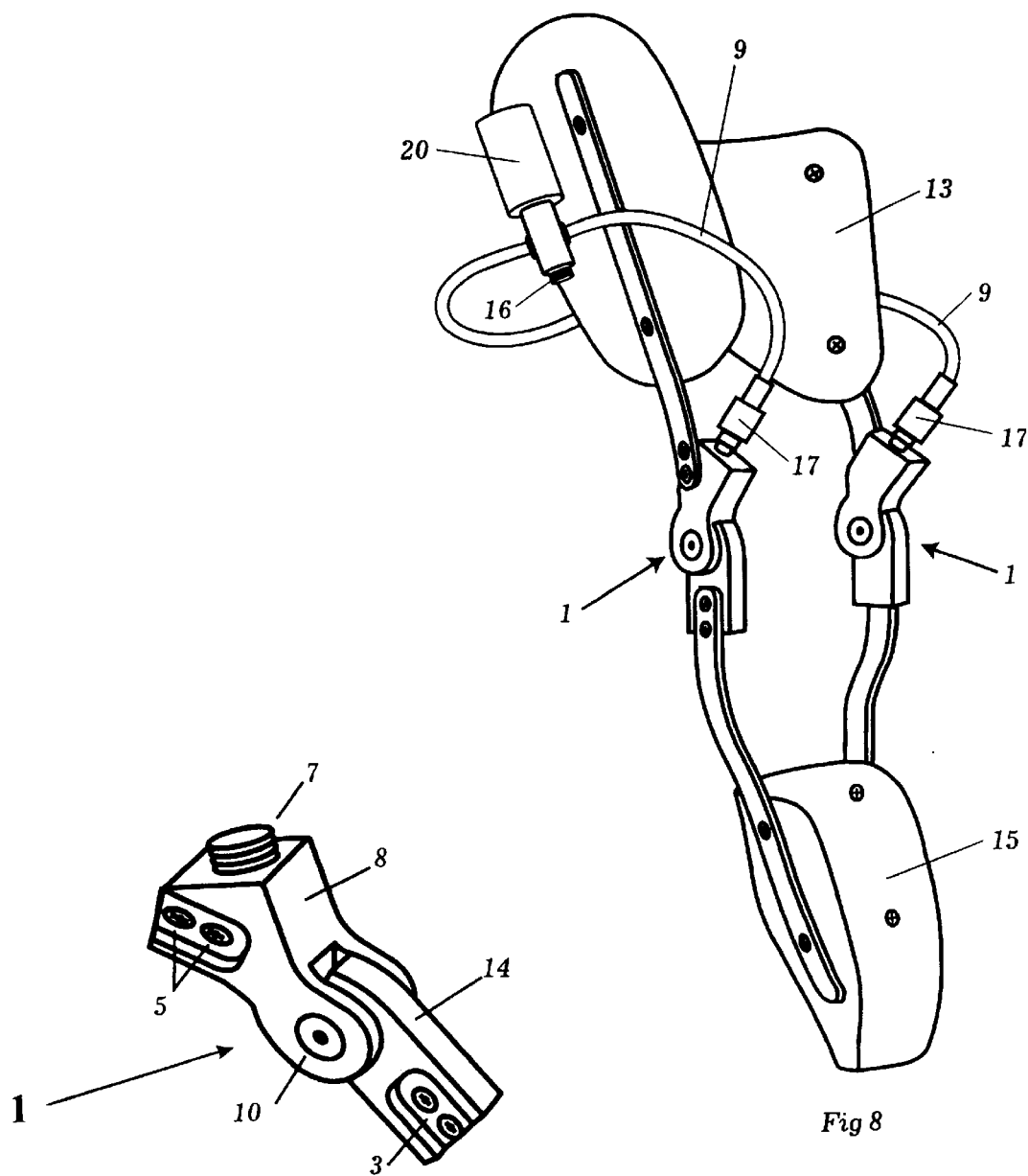
FIG. 1 is a perspective view of the proximal and distal joint members of the preferred embodiment of the present invention being connected to one another at a pivot point.
FIG. 8 is a perspective view of two proximal joint members and two distal joint members forming two separate present invention joints that are laterally connected between cooperating parts of an orthotic device used for support of a human knee, with both proximal joint members connected by separate fluid supply lines to opposing fluid ports on a single hydraulic intensifier.

FIG. 1 shows the preferred embodiment of a joint 1 comprising a proximal joint member 8 and a distal joint member 14 connected to one another at pivot point 10, so that proximal joint member 8 and distal joint member 14 each have a pivoting end and an opposed attachment end. The pivoting end of distal joint member 14 is connected within a U-shaped cut-out in the pivoting end of proximal joint member 8, the U-shaped cut-out being configured to allow free movement of distal joint member 14 relative to stationary proximal joint member 8 between a position of maximum extension and a position of maximum flexion, respectively illustrated in FIGS. 3–5. FIG. 1 shows the attachment end of distal joint member 14 having a bar slot 3 with two attachment holes 5. FIG. 1 also shows the attachment end of proximal joint member 8 having one bar slot 3 with two attachment holes 5, but further shows proximal joint member 8 having a male hydraulic fitting 7 used for the connection of proximal joint member 8 to a fluid supply line (shown as number 9 in FIG. 8) for the introduction of linear hydraulic forces (not shown) into a ball bearing race (shown as number 12 in FIGS. 2–5 and in FIG. 9, but not shown in FIG. 1) that extends longitudinally within proximal joint member 8. The placement, number, dimension, and configuration of bar slots 3 and attachment holes 5 in both proximal joint member 8 and distal joint member 14 are not critical to the present invention, and would vary according to the intended use to provide secure attachment of each joint 1 between the cooperating parts of a device requiring pivotal movement, such as upper brace 13 and lower brace 15 which are shown in FIG. 8. Cosmetic considerations would also be a factor in selecting the placement, number, dimension, and configuration of bar slots 3 and attachment holes 5. Further, although not shown, it is also contemplated for the present invention to have attachment means other than bar slots 3 and attachment holes 5 which would securely and discretely connect the attachment ends of proximal joint member 8 and distal joint member 14 to objects such as upper brace 13 and lower brace 15 to allow extension assist for lower brace 15 and controlled flexion flow between upper brace 13 and lower brace 15.

Figure 9:
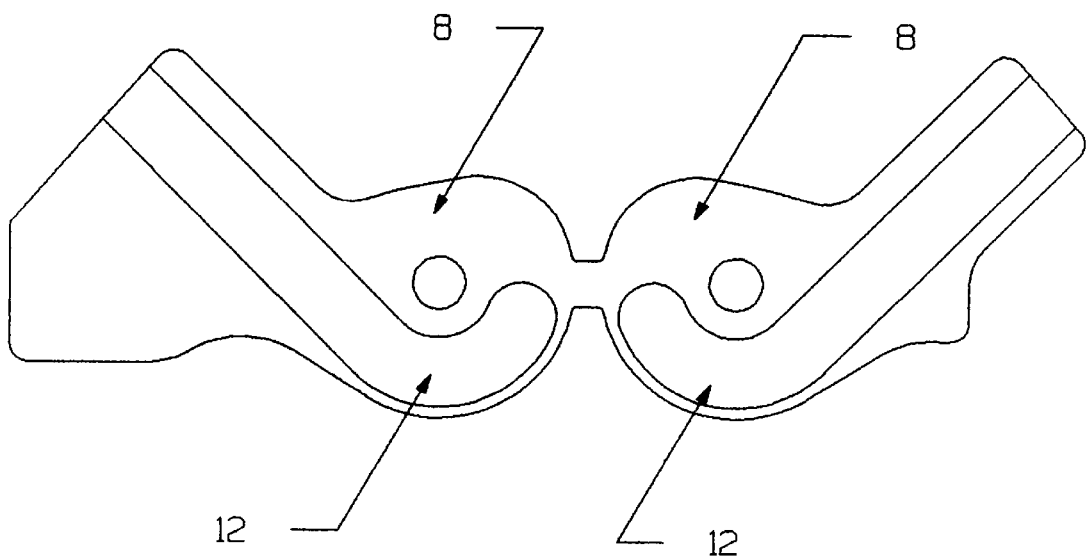
FIG. 9 is an interior view of the proximal joint member of the present invention as it appears during manufacture after the step of ball bearing race formation and prior to the step in which the two proximal joint member pieces are bonded together.

In the preferred embodiment of the present invention, and as further shown in FIG. 9, it is contemplated for proximal joint member 8 to have a two-piece construction for ease in forming the partially arcuate ball bearing race 12 (shown in FIGS. 2–5 and 9). FIG. 1 and FIG. 9 both illustrate one side of proximal joint member 8 as having a substantially Y-shaped configuration, with the downwardly depending stem of the Y-shape having a substantially circular perimeter on its end and pivot point 10 positioned centrally within that circular perimeter to form substantially one-half of the pivoting end of proximal joint member 8 that includes the U-shaped cutout within which the pivoting end of distal joint member 14 is positioned for rotation during use. The two upwardly extending arms of the Y-shaped proximal joint member 8 each help to form the attachment end of proximal joint member 8 and respectively contain bar slot 3 and male hydraulic fitting 7. Although not shown, it is also within the scope of the present invention for both sides of proximal joint member 8 to have configurations different from that shown in FIG. 9, or even an identical configuration, depending upon the intended use. However, for orthotic use and other uses in which the maximum weight of joint 1 is a design consideration, only one side of proximal joint member 8 would have a widened attachment end configuration, such as the Y-shaped configuration shown in FIGS. 1 and 9. The means for connecting distal joint member 14 within the U-shaped cutout in proximal joint member 8 at pivot point 10 is not critical as long as the connecting means creating pivot point 10 is configured and dimensioned to be sufficiently strong for the contemplated use, such as when joint 1 would be used to support a human knee. The materials used for constructing distal joint member 14 and proximal joint member 8 are also not critical as long each is sufficiently strong for the use contemplated.

Figure 2:
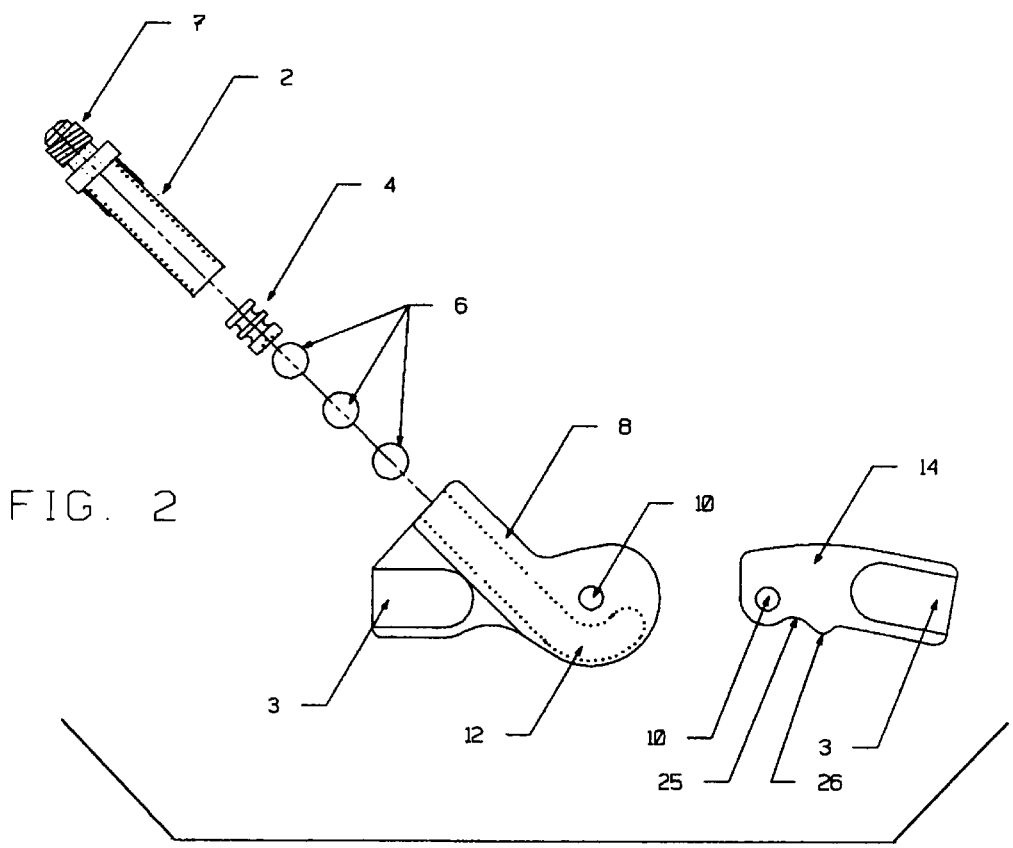
FIG. 2 is an exploded sectional side view of the preferred embodiment of the present invention having a proximal joint member and a distal joint member poised for pivoting connection to one another, as well as a proximal fluid tube, plunger, and ball bearings poised for insertion within a partially arcuate race in the proximal joint member where they help effect the radial hydraulic force transfer achieved in the present invention joint during use.

FIG. 2 shows the present invention having proximal joint member 8 and distal joint member 14 poised for pivoting connection to one another at their respective pivot points 10. FIG. 2 also shows proximal joint member 8 and a distal joint member 14 each having one bar slot 3 on its respective attachment end for use in connecting proximal joint member 8 and distal joint member 14 between the cooperating parts of a device requiring pivotal movement, such as the orthotic device shown in FIG. 8. Although not shown in FIG. 2, it is contemplated to have a plurality of attachment holes 5 through bar slots 3, or other means for securely and discretely attaching an orthotic or other device requiring pivotal movement to bar slots 3 during use. In addition, FIG. 2 shows distal joint member 14 having an indentation 25 adjacent to pivot point 10 that is positioned to interact during extension assist with the innermost ball bearing 6 positioned within ball bearing race 12 which extends longitudinally through proximal joint member 8. In the preferred embodiment it is contemplated for the perimeter of indentation 25 to have a radius of curvature similar to that of ball bearings 6 so that indentation 25 can remain in close contact with ball bearings 6 during extension of joint 1. FIG. 2 also shows distal joint member 14 having a protrusion 26 positioned adjacent to indentation 25, with protrusion 26 being positioned between indentation 25 and the attachment end of distal joint member 14. Protrusion 26 is strategically positioned to interact during flexion with the ball bearings 6 positioned within race 12 to force ball bearings 6 from the arcuate portion of race 12 and into the linear portion of race 12 adjacent to male hydraulic fitting 7. The length of the linear portion of race 12 and the number of ball bearings 6 used will determine the amplitude of extension possible for distal joint member 14 relative to proximal joint member 8. In contrast, the length of the arcuate portion of race 12 and the number of ball bearings 6 used will affect the amount of flexion flow possible for distal joint member 14 relative to proximal joint member 8. Acting in combination with plunger 4, protrusion 26 and indentation 25 provide the means by which ball bearings 6 are retained within the otherwise open-ended race 12. The diameter of race 12 is shown in FIG. 2 to have a uniform dimension throughout its entire length.

FIG. 2 further shows the ball bearing race 12 in proximal joint member 8 having a J-shaped configuration with an arcuate end that partially curves around pivot point 10. As shown in FIG. 9, for ease in the formation of race 12, it is contemplated for proximal joint member 8 to be formed by two-piece construction, with each side of proximal joint member 8 comprising substantially one-half of race 12 before being bonded together to create a finished proximal joint member 8 ready for use. FIG. 2 further shows three aligned ball bearings 6 ready for insertion into race 12, with each ball bearing 6 having a diameter dimension slightly smaller than the diameter dimension of race 12, as well as proximal fluid tube 2 shown ready for insertion within the linear end of race 12. The number of ball bearings 6 used is not critical and it is contemplated for joint 1 to comprise a number of ball bearings 6 that is suitable to its size and to the function to which it will be applied. In addition, FIG. 2 shows male hydraulic fitting 7 connected to one end of proximal fluid tube 2 and a plunger 4 poised for insertion within the other end of proximal fluid tube 2. During use, plunger 4 will remain in contact with the aligned ball bearing 6 most closely positioned to male hydraulic fitting 7. It is contemplated for plunger 4 to be configured for slidable but fluid-tight positioning within proximal fluid tube 2, so as to help maintain the hydraulic pressure within proximal fluid tube 2 for extension assist of distal joint member 14. Although not shown, upon introduction of increased hydraulic force into proximal fluid tube 2, plunger 4 will be caused to engage ball bearings 6 and move them into the arcuate end of race 12, thereby radially transferring the hydraulic force applied. Since for ease of manufacture it is contemplated for proximal joint member 8 to be made from two-piece construction, in the preferred embodiment the fluid-tight environment necessary for effective application of hydraulic force on ball bearings 6 would be provided by the combination of proximal fluid tube 2, plunger 4, and male hydraulic fitting 7.

Figure 3:
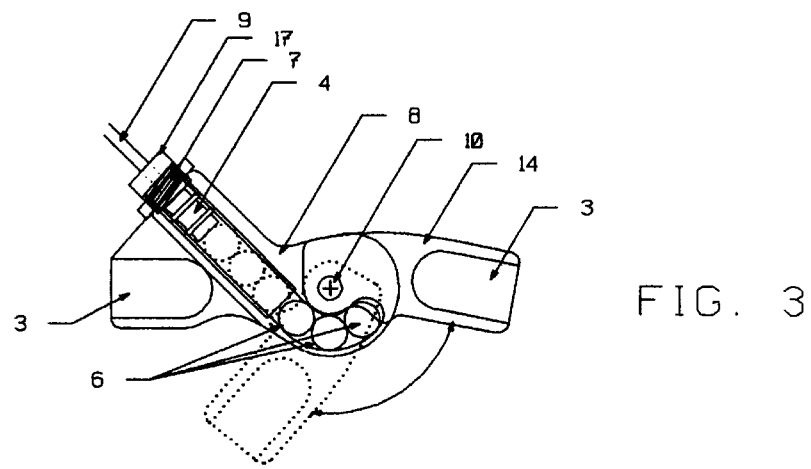
FIG. 3 is a sectional side view of the preferred embodiment of the present invention having a proximal joint member and a distal joint member pivotally connected to one another with an arrow showing the approximate amplitude of movement of the rotating distal joint member relative to the stationary proximal joint member, with the solid line depiction of the distal joint member and ball bearings illustrating a position of near maximum extension, and the dotted line depiction of the distal joint member and ball bearings illustrating a position of near maximum flexion.

FIG. 3 shows the present invention having proximal joint member 8 and distal joint member 14 connected together at pivot point 10. FIG. 3 shows proximal joint member 8 and distal joint member 14 each having a bar slot 3 on its attachment end for use in connecting proximal joint member 8 and distal joint member 14 between the cooperating parts of a device requiring pivotal movement, such as the orthotic device shown in FIG. 8. Race 12 extends longitudinally through proximal joint member 8 and has a partially arcuate, J-shaped configuration. Proximal fluid tube 2 is positioned within the linear end of race 12, with plunger 4 and ball bearings 6 also positioned within proximal fluid tube 2 so that plunger 4 is between ball bearings 6 and the attachment end of proximal joint member 8. In the preferred embodiment of the present invention, it is contemplated for male hydraulic fitting 7 to have a threaded configuration and be attached to the end of proximal fluid tube 2 remote from pivot point 10. Male hydraulic fitting 7 is also connected to proximal fluid tube 2 so that its threaded end extends beyond the attachment end of proximal joint member 8. FIG. 3 further shows a female hydraulic fitting 17 connected over the threaded end of male hydraulic fitting 7, with an hydraulic fluid supply line 9 connected to female hydraulic fitting 17 for the introduction of hydraulic force (not shown) into proximal fluid tube 2 upon demand. In FIG. 3 solid lines show the movable distal joint member 14 and ball bearings 6 in positions of near maximum extension relative to stationary proximal joint member 8. However, dotted lines in FIG. 3 also illustrate movable distal joint member 14 in a position of near maximum flexion relative to proximal joint member 8 with dotted lines also showing the position ball bearings 6 would assume within proximal fluid tube 2 in this position of near maximum distal joint member 14 flexion. FIG. 3 further comprises an arrow which shows the approximate amplitude of movement of the rotating distal joint member 14 relative to the stationary proximal joint member 8 between positions of near maximum extension and near maximum flexion. In FIG. 3, ball bearings 6 are shown to be in contact with distal joint member 14 during both extension and flexion movement of distal joint member 14 relative to proximal joint member 8.

FIGS. 4 and 5 more clearly show joint 1 in positions of near maximum flexion and near maximum extension, respectively. Both FIGS. 4 and 5 show proximal joint member 8 and distal joint member 14 pivotally connected to one another at pivot point 10, proximal fluid tube 2 positioned within race 12, plunger 4 positioned within proximal fluid tube 2, male hydraulic fitting 7 connected to proximal fluid tube 2 and extending beyond the attachment end of proximal joint member 8, female hydraulic fitting 17 connected to male hydraulic fitting 7, fluid supply line 9 connected to female hydraulic fitting 17, and bar slots 3 cut into the side surfaces of both proximal joint member 8 and distal joint member 14 on their respective attachment ends for use in connecting joint 1 between the cooperating members of a device requiring a movable joint, such as upper brace 13 and lower brace 15 of the orthotic device shown in FIG. 8. FIGS. 4 and 5 further show a protrusion 26 on the flexion side of distal joint member 14 near to its pivoting end and an indentation 25 positioned between protrusion 26 and pivot point 10. As shown in FIG. 5, in the preferred embodiment of joint 1 it is contemplated for indentation 25 to have a dimension and arcuate configuration substantially similar to that of ball bearings 6. Thus, as in FIG. 4 when distal joint member 14 is in a position of near maximum flexion, plunger 4 is positioned adjacent to male hydraulic fitting 7 with all three ball bearings 6 situated within proximal fluid tube 2, and held in place by protrusion 26. Conversely, in FIG. 5 when distal joint member 14 is in a position of near maximum extension, plunger 4 is positioned within the interior end of proximal fluid tube 2 located adjacent to pivot point 10, and all three ball bearings 6 are positioned beyond this interior end, within the arcuate portion of race 12, with the ball bearing 6 most remote from proximal fluid tube 2 shown aligned with indentation 25 and resting against it. Thus FIGS. 3–5 show plunger 4 acting in combination with indentation 25 and protrusion 26 to retain ball bearings 6 within race 12 during flexion and extension of distal joint member 14 relative to proximal joint member 8.

Figure 6:
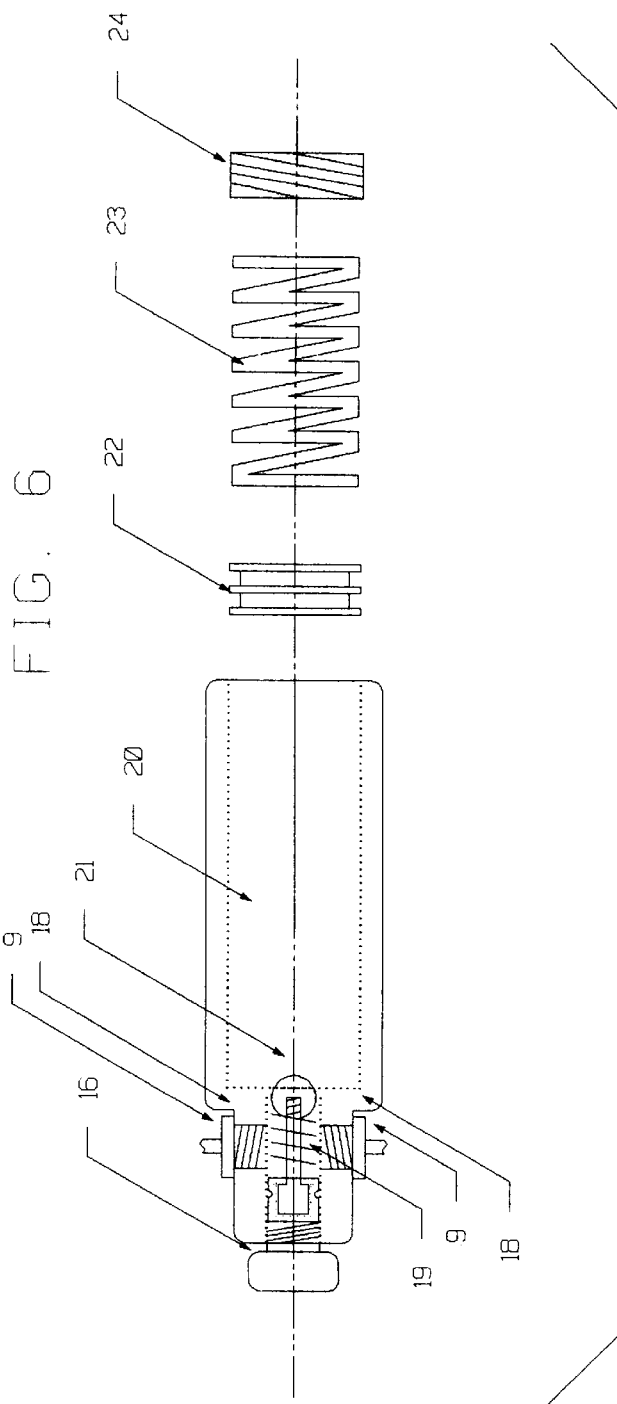
FIG. 6 is an exploded sectional view of the preferred means for introducing hydraulic forces into the linear end of the partially arcuate ball bearing race within the proximal joint member of the present invention.
Figure 7:
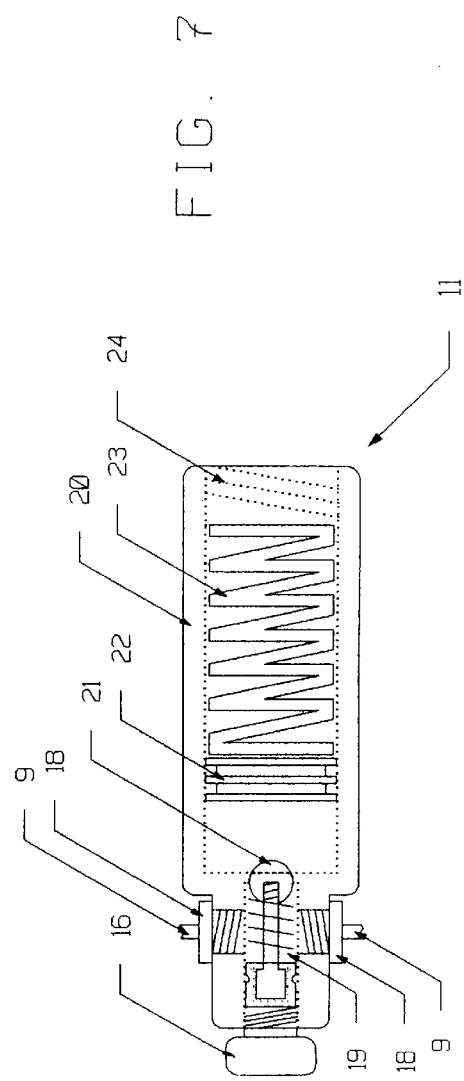
FIG. 7 is a sectional view of the preferred means for introducing hydraulic forces into the ball bearing race of the present invention having a heavy duty spring, a piston, opposed fluid ports, a manual fluid flow adjustment control, and a one-way check valve.

FIGS. 6 and 7 show the preferred assembly 11 for introducing hydraulic forces into race 12 of joint 1 so that distal joint member 14 is assisted in its movement relative to proximal joint member 8 between positions of maximum flexion and extension. Assembly 11 is also configured to provide controlled flexion flow of distal joint member 14 relative to proximal joint member 8, as well as an infinite number of flexion stops. FIG. 6 shows piston 22 and a heavy duty spring 23 ready for insertion within the open end of the hydraulic intensifier 20, with a threaded cap 24 ready for connection to female threads around the open end of hydraulic intensifier 20 so that sufficient adjustable spring force can be provided to apply hydraulic force (not shown) to ball bearings 6 (shown in FIGS. 2–5) and thereby allow the desired amount of extension assist, as well as flexion control, in joint 1. FIGS. 6 and 7 also show two fluid ports 18 connected through the side walls of hydraulic intensifier 20 near to the end of hydraulic intensifier 20 opposed from threaded cap 24. Starting at a position of maximum flexion (as shown in FIGS. 3 and 4) distal joint member 14 would be positioned against ball bearings 6, with ball bearings 6 being almost entirely contained within proximal fluid tube 2 in the linear end of race 12. As distal joint member 14 is extended rotatably around proximal joint member 8 at pivot point 10 toward a position of maximum extension, ball bearings 6 are allowed by distal joint member 14 to move incrementally into the arcuate end of race 12, so that at a position of maximum extension, ball bearings 6 are almost entirely positioned beyond the interior end of proximal fluid tube 2. As ball bearings 6 remain in contact with distal joint member 14 and move within race 12 toward its arcuate end, the interior volume of proximal fluid tube 2 available for containing hydraulic fluid (not shown) is expanded and the hydraulic pressure within proximal fluid tube 2 correspondingly drops. Such hydraulic pressure decrease allows heavy duty spring 23 to force additional hydraulic fluid past one-way check valve 21, through ports 18, and into fluid supply lines 9 to flood proximal fluid tube 2, increase the hydraulic pressure within proximal fluid tube 2 to sustain extension assist and further keep plunger 4 in contact with ball bearings 6, and ball bearings 6 in contact with indentation 25. The constant adjustable spring force, through linear hydraulic application, is thereby transferred into the radial movement of distal joint member 14 around pivot point 10. When an outside flexion force is applied to distal joint member 14, such as the force exerted by the weight of a person being shifted forward over joint 1 in the application of joint 1 being used in an orthotic device to support a person's knee, distal joint member 14 forces ball bearings 6 incrementally back into proximal fluid tube 2 and two separate actions may occur depending on the open, closed, or partially closed position of fluid flow adjustment control 16. First, when fluid flow adjustment control 16 is turned in a clockwise direction, valve return spring 19 will hold one-way check valve 21 in a position to restrict fluid flow (not shown) back into hydraulic intensifier 20, thereby preventing distal joint member 14 from rotating in a flexion direction. Second, when fluid flow adjustment control 16 is turned in a counter-clockwise direction, valve return spring 19 will be overpowered by the fluid flow, thereby allowing varying amounts of fluid to by-pass one-way check valve 21 and return to hydraulic intensifier 20 and causing a flexion moment to occur between proximal joint member 8 and distal joint member 14. In the preferred embodiment, although not critical to the present invention, the materials used for hydraulic intensifier 20, piston 22, and threaded cap 24 would be aluminum with a hard coating thereon to improve its durability and longevity. Also in the preferred embodiment, one-way check valve 21 would be manufactured from brass and stainless steel to create a tight seating valve, and all seals would be rubber "o" rings. Further in the preferred embodiment of the present invention, hydraulic intensifier 20 would have an outside diameter of approximately one-and-one-half inches, a length of approximately five inches, and a reamed interior having an approximate diameter dimension of one-and-one-eighth inches. Also, although not shown, it is within the scope of the present invention to provide additional means for creating spring force on the hydraulic fluid, such as the use of an air pressure accumulator. When threaded cap 24 is secured within the female threaded end of hydraulic intensifier 20, in the preferred embodiment of the present invention spring 23 is contemplated to be a heavy duty compression spring that is positioned between threaded cap 24 and one end of piston 22 so that piston 22 can slidably move within hydraulic intensifier 20 to provide the desired amount of hydraulic force interaction with ball bearings 6 (shown in FIGS. 2–5) for the level of extension assist required for joint 1 in each intended use. As fluid flow adjustment control 16 is rotated, it selectively engages valve return spring 19 to change the position of a ball valve 21 relative to fluid ports 18 and allows differing amounts of hydraulic fluid (not shown) through each fluid port 18 and into the fluid supply line 9 attached between each port 18 and the female hydraulic fittings 17 in communication with proximal fluid tubes 2.

FIG. 8 shows two joints 1 connected laterally between an upper brace 13 and a lower brace 15 which are configured for use in supporting and assisting the movement of a human knee (not shown). FIG. 8 shows a separate fluid supply line 9 connected between each joint 1 and opposing sides hydraulic intensifier 20, with connection of fluid supply lines 9 to each joint 1 being accomplished through connection of female hydraulic fitting 17 to male hydraulic fitting 7 (as shown in FIGS. 1 and 2). FIG. 8 further shows hydraulic intensifier 20 having fluid flow adjustment control 16 connected thereto for allowing selective amounts of hydraulic force into proximal fluid tubes 2 to interact with ball bearings 6 (shown in FIGS. 3–5) to cause extension assist and flexion flow with infinite controlled stops in the movement of upper brace 13 relative to lower brace 15.

FIG. 9 shows the preferred means for creating race 12 in proximal joint member 8. Although not critical to the manufacture of proximal joint member 8 but to facilitate it, as shown in FIG. 9, proximal joint member 8 would be formed from two individually machined pieces of material, each of which has approximately one-half of race 12 cut therein before the two pieces are bonded together to create proximal joint member 8. It is not critical to the present invention whether the race 12 in each piece is separately or simultaneously machined relative to its mated piece. The bonding means used to secure the two pieces together is not critical to the present invention as long as it provides for a strong adhesive bond able to withstand the weight transfer forces that would be applied to it during use in supporting a human knee. The materials and dimension of assembly 11 and joint 1 would both be selected according to the intended use of the present invention.

To use the preferred embodiment of the present invention shown in FIGS. 1–9 for orthotic use in support of a human knee, two joints 1 would be used and made from durable materials able to withstand the repeated stress caused by rotational movement of distal joint member 8 relative to proximal joint member 14 under a load equivalent to the body weight of its heaviest anticipated user (not shown). One would laterally attach upper brace 13 to the bar slots 3 on each of the attachment ends of the two proximal joint members 8 used, and also laterally attach lower brace 15 to the bar slots 3 on the attachment ends of each of the two distal joint members 14. A single assembly 11 would be attached to upper brace 13 in a position easily accessible to the user and connected to both joints 1 through independent fluid supply lines 9. Assembly 11 could then be readily manipulated as needed by the user to allow variable extension assist of lower brace 15 relative to upper brace 13, free action of lower brace 15 relative to upper brace 13 with pressure return, or a full lock against motion of lower brace 15 relative to upper brace 13. Rotation of fluid flow adjustment control 16 in a clockwise direction would allow spring 23 to increase hydraulic pressure upon ball bearings 6 to move them into the arcuate portion of race 12 to cause radial hydraulic force transfer and forward movement of lower brace 15 relative to upper brace 13. For controlled flexion movement with infinite flexion stops, clockwise movement of fluid flow adjustment control 16 would also cause valve return spring 19 to hold one-way check valve 21 in a position that restricts fluid flow back into hydraulic intensifier 20, thereby preventing flexion rotation of distal joint member 14. In contrast, counter-clockwise rotation of fluid flow adjustment control 16 would cause valve return spring 19 to become increasingly overpowered, wherein hydraulic fluid (not shown) would by-pass one-way check valve 21 and return to hydraulic intensifier 20, causing a flexion moment to occur between proximal joint member 8 and distal joint member 14.

What is claimed is:

1. An orthotic joint for providing extension assist for the radial movement of a rotating member relative to a stationary member in a device requiring pivotal movement, said orthotic joint comprising:

a proximal joint member having a partially arcuate race extending longitudinally therethrough, a pivoting end, and an opposed attachment end;

a distal joint member having a pivoting end, and an opposed attachment end;

pivotal connection means for attaching said pivoting ends of said proximal joint member and said distal joint member to one another at a pivot point for free rotation of said distal joint member relative to said proximal joint member between a position of maximum flexion and a position of maximum extension;

a plurality of ball bearings positioned within said race, said ball bearings dimensioned slightly smaller than said race for free movement within said race; and hydraulic force introduction means adapted for applying selected variable amounts of linear hydraulic force against said ball bearings in said race so that said applied linear hydraulic force becomes radially transferred, and when the rotating member in a device requiring pivotal movement is connected to said attachment end of said distal joint member and the stationary member in the device requiring pivotal movement is connected to said attachment end of said proximal joint member, said radially transferred hydraulic force provides the rotating member with extension assist as it moves toward said position of maximum extension.

2. The orthotic joint of claim 1 wherein said race comprises an arcuate end and a linear end, wherein said hydraulic force introduction means comprises a proximal fluid tube positioned within said linear end of said race with said proximal fluid tube having an attachment end, a fluid supply line with opposing ends and one of said opposing ends connected to said attachment end of said proximal fluid tube for fluid communication between said fluid supply line and said proximal fluid tube, a plunger configured for slidable but fluid-tight positioning within said proximal fluid tube with said plunger being positioned between said ball bearings and said attachment end of said proximal fluid tube, and wherein said hydraulic force introduction means also comprising a hydraulic intensifying assembly configured to provide adjustable extension assist and flexion flow of said distal joint member with an infinite number of flexion stops, said assembly being connected to and in fluid communication with the other of said opposing ends of said fluid supply line.

3. The orthotic joint of claim 2 wherein said hydraulic intensifying assembly comprises a hydraulic intensifier having an exterior wall, opposite ends, and a hollow interior with a piston and a heavy duty spring positioned within said interior, at least one fluid port communicating through said exterior wall, said piston being positioned between said spring and said fluid port, a fluid flow adjustment control connected to the one of said opposite ends of said hydraulic intensifier remote from said spring, and a one-way valve positioned between said adjustment control and said fluid port so that upon selective engagement of said adjustment control said spring and said one-way valve will allow varying amounts of hydraulic fluid to flow from said interior and through said fluid port for differing amounts of both extension assist and controlled flexion flow of said distal joint member during radial movement of said distal joint member around said pivot point.

4. The orthotic joint of claim 3 further comprising at least one additional proximal joint member, a corresponding number of additional distal joint members so that one of said additional distal joint members is available for each of said additional proximal joint members provided, a corresponding number of additional fluid supply lines so that one of said additional fluid supply lines is available for connection to each of said additional proximal joint members provided, and a corresponding number of additional fluid ports in said hydraulic intensifier so that one of said additional fluid ports is available for connection to each of said additional fluid supply lines provided so that said distal joint member and said additional distal joint members can act in unison with said hydraulic intensifying assembly to provide extension assist and controlled flexion flow between the cooperating parts of a device requiring pivotal movement.

5. The orthotic joint of claim 3 wherein said hydraulic intensifier, said distal joint member, and said proximal joint member are each compactly configured to provide discrete and unobtrusive connection between the cooperating parts of a device requiring pivotal movement.

6. The orthotic joint of claim 2 wherein said hydraulic intensifying assembly comprises air accumulator means for providing in part said linear hydraulic force applied to said ball bearings.

7. The orthotic joint of claim 1 wherein said distal joint member has a flexion side, and a protrusion on said flexion side, said distal joint member also having an indentation on said flexion side between said protrusion and said pivoting end of said distal joint member, said protrusion having a configuration adapted for keeping said ball bearings within said race during flexion of said distal joint member relative to said proximal joint member, and said indentation having a configuration adapted for keeping said ball bearings within said race during extension of said distal joint member relative to said proximal joint member.

8. The orthotic joint of claim 1 wherein said race is J-shaped.

9. The orthotic joint of claim 1 wherein said proximal joint member is formed from two separate pieces bonded together with each of said pieces having approximately one-half of said race longitudinally incised therein.

10. The orthotic joint of claim 9 wherein one of said pieces has a substantially Y-shaped configuration with a downwardly depending stem and two upwardly extending arms, and said stem partially comprises said pivoting end of said proximal joint member and said arms partially comprise said attachment end of said proximal joint member.

11. The orthotic joint of claim 1 wherein said pivoting end of said proximal joint member has a U-shaped cut-out within which said pivoting end of said distal joint member is connected for rotation at said pivot point.

12. The orthotic joint of claim 1 further comprising at least one bar slot on said attachment end of said distal joint member and at least one bar slot on said attachment end of said proximal joint member, and a plurality of attachment holes through each of said bar slots adapted for connection of said distal joint member and said proximal joint member the cooperating parts of a device requiring pivotal movement.

13. An orthotic joint which is compact in configuration and dimension, and which can be used alone or in combination to discretely provide both variable extension assist and controlled flexion flow with an infinite number of flexion stops to a first object requiring pivotal movement relative to a stationary second object, said orthotic joint comprising:

a compactly configured proximal joint member having an open-ended race with an arcuate end and a linear end;

a compactly configured distal joint member rotationally connected to said proximal joint member at a pivot point;

pivotal connection means attached between said proximal joint member and said distal joint member, said pivotal connection means being adapted to permit free movement of said distal joint member relative to said proximal joint member between positions of maximum extension and maximum flexion;

a plurality of ball bearings configured and dimensioned for aligned movement within said race, said ball bearings being moved toward said arcuate end of said race when said distal joint member is caused to move toward said position of maximum extension; and a compactly configured hydraulic force introduction means adapted for easily and discretely providing varying amounts of linear hydraulic force against said ball bearings so that when at least one of said distal joint members is connected to a first object requiring pivotal movement, an identical number of said proximal joint members are connected to a stationary second object, said ball bearings are positioned within each of said races, and said hydraulic force introduction means is connected for communication with said linear ends of each of said races being used, said hydraulic force introduction means may be adjusted by a user to introduce an essentially identical selected amount of linear hydraulic force into each of said races wherein said linear hydraulic force is caused to be radially transferred through all of said ball bearings for assisted extension of the first object relative to the second object between said position of maximum flexion and said position of maximum extension, and so that adjustment of said hydraulic force introduction means also provides the first object with controlled flexion flow between said position of maximum extension and said position of maximum flexion as well as an infinite number of flexion stops.

14. The orthotic joint of claim 13 further comprising a proximal fluid tube positioned within said linear end of said race and a plunger positioned within said proximal fluid tube between said hydraulic force introduction means and said ball bearings; and wherein said linear end of said race is elongated and said arcuate end depends from said linear end; said linear end and said arcuate end both have a uniform and identical diameter dimension; and said distal joint member is configured to remain in contact the one of said ball bearings nearest to said pivot point during both extension and flexion flow of said distal joint member so that hydraulic force applied against said plunger will move said plunger and said ball bearings between a position of maximum flexion where all of said ball bearings are substantially contained within said proximal fluid tube, and a position of maximum extension where substantially all of said ball bearings are positioned beyond said proximal fluid tube and within said race.

15. The orthotic joint of claim 14 wherein said hydraulic force introduction means comprises an essentially cylindrical hydraulic intensifier having a hollow interior and opposite ends with a heavy duty compression spring dimensioned for movement within said hollow interior, at least one fluid port centrally communicating through said hydraulic intensifier, a piston positioned between said spring and said port, an adjustable valve control connected through said hydraulic intensifier, a one-way valve connected to said control wherein said one-way valve is positioned between said port and said control so that when said distal joint member is extended and said control is adjusted in a clockwise direction, lowered pressure in said race will allow said spring to move said piston toward said port and increase the amount of hydraulic fluid entering said proximal fluid tube to provide extension assist to said distal joint member, and clockwise adjustment of said control during flexion will cause said valve to restrict hydraulic fluid flow back into said hydraulic intensifier thereby preventing flexion movement of said distal joint member, while counter-clockwise rotation of said control allows said valve to become overpowered and allow controlled flexion flow of said distal joint member at varying levels of pressure return.

16. The orthotic joint of claim 15 wherein said distal joint member further comprises a flexion side, an indentation on said flexion side, and a protrusion positioned on said flexion side with said indentation being positioned between said protrusion and said pivot point, said indentation having a radius of curvature substantially similar to that of said ball bearings to allow said distal joint member to remain in contact with the innermost of said ball bearings during extension, and said protrusion being configured to allow said distal joint member to remain in contact with the innermost of said aligned ball bearings during flexion.

17. A method for providing radial hydraulic force transfer which allows both variable extension assist and controlled flexion flow with an infinite number of flexion stops between two cooperating parts of a device requiring pivoting movement, said method comprising the steps of:

provM a pivoting distal joint member with a substantially linear configuration and a stationary proximal joint member with a partially arcuate race longitudinally therethrough;

also providing a plurality of ball bearings, a number of proximal fluid tubes identical to the number of orthotic joints provided, a number of plungers identical to the number of orthotic joints provided, a hydraulic intensifier with spring means capable of providing hydraulic force which comprises a valve and a valve control, a first object requiring pivotal movement, and a stationary second object;

attaching each of said orthotic joints between said first object and said second object so that each of said distal joint members is connected to said first object and each of said proximal joint members is connected to said stationary second object;

attaching said hydraulic intensifier in a position on said second object so that said valve control is easily accessible to a user for adjustment of the amount of hydraulic force leaving said hydraulic intensifier and being introduced into all of said races provided;

inserting each of said proximal fluid tubes into a different one of said races;

inserting an equivalent number of said ball bearings into each one of said races provided so that said ball bearings can move into said proximal fluid tubes during flexion movement of said distal joint members;

inserting each of said plungers into a different one of said proximal fluid tubes so that said plungers are in contact with said ball bearings, said plungers being configured so that said plungers each provide a fluid-tight hydraulic seal during movement within one of said proximal fluid tubes;

placing said hydraulic intensifier in hydraulic communication with each of said proximal fluid tubes; and using said valve control to adjust the amount of said linear hydraulic force flowing into each of said proximal fluid tubes and allowing all of said plungers provided to simultaneously move said ball bearings toward said arcuate ends of said races to cause radial hydraulic force transfer and extension assist when said first object is moved toward a position of maximum extension relative to said second object, and during flexion flow of said distal joint member to cause adjustable amounts of pressure return as well as an infinite number of flexion stops.

18. The method of claim 17 further comprising the steps of providing orthotic joints each having a race that is J-shaped and distal joint members having a proximal side with an indentation and a protrusion positioned adjacent to one another on said proximal side, said indentation being configured and positioned to remain in contact with and keep said ball bearings within said race during extension, and said protrusion being configured and positioned to remain in contact with said ball bearings and keep said ball bearings within said race during flexion.

* * * * *